United States Patent [19]

Imperante et al.

[11] Patent Number: 5,382,381
[45] Date of Patent: Jan. 17, 1995

[54] ALKOXYLATED SILICONE PHOSPHATE ESTERS AS EMULSIFIERS

[75] Inventors: John Imperante, 4 Lance Rd., Lebanon, N.J. 08833; John H. Hannon, Park Ridge, N.J.

[73] Assignee: John Imperante, Somerville, N.J.

[21] Appl. No.: 995,385

[22] Filed: Dec. 14, 1992

[51] Int. Cl.$^6$ .............................................. B01D 13/00
[52] U.S. Cl. ..................................... 252/312; 252/314; 424/59; 514/941; 514/939; 514/75
[58] Field of Search ....................... 252/312, 314, 351; 424/59; 514/938, 939, 941, 75, 77

[56] References Cited

U.S. PATENT DOCUMENTS

| | | | |
|---|---|---|---|
| 5,070,171 | 12/1991 | O'Lenick, Jr. | 528/33 |
| 5,091,493 | 2/1992 | O'Lenick, Jr. | 528/30 |
| 5,093,452 | 3/1992 | O'Lenick, Jr. | 528/25 |
| 5,232,688 | 8/1993 | Ziegler et al. | 424/59 |
| 5,288,814 | 2/1994 | Long, II et al. | 525/450 |
| 5,302,378 | 4/1994 | Crotty et al. | 424/59 |
| 5,332,569 | 7/1994 | Wood et al. | 514/937 X |

OTHER PUBLICATIONS

McCutcheon's 1992, vol. 2, Functional Materuals North American International Edition, (McCutcheon's division, MC Publishing Co., Glen Rock, N.J., 1992) pp. 57, 62, 68.
Greenberg et al., Handbook of Cosmetic Materials, (Interscience Publishers, Inc., 1954) pp. 28(9), 58(9), 140(1), 164(5), 189, 213.

Primary Examiner—Robert L. Stoll
Assistant Examiner—Daniel S. Metzmaier

[57] ABSTRACT

The present invention relates to a process for the preparation of stable oil in water emulsions which comprises (a) mixing an oil with effective emulsifying concentration of a silicone based phosphate ester (b) subsequently adding water and in a final step (c) homogenizing the resulting mixture to obtain a surprisingly stable emulsion.

10 Claims, No Drawings

ALKOXYLATED SILICONE PHOSPHATE ESTERS AS EMULSIFIERS

BACKGROUND OF THE INVENTION

FIELD OF INVENTION

The present invention relates to a process for the preparation of stable oil in water emulsions which comprises (a) mixing an oil with effective emulsifying concentration of a silicone based phosphate ester (b) subsequently adding water and in a final step (c) homogenizing the resulting mixture to obtain an surprisingly stable emulsion which does not contain any fatty surfactants.

The process of the present invention is made possible by using certain compounds of which are prepared by the phosphation of a pendant hydroxyl group which is present on a silicone polymer and which contains at least three moles of ethylene oxide in the molecule. In a preferred embodiment the process is conducted using a silicone based phosphate ester which is based upon a hydroxy containing silicone polymer that has been alkoxylated with ethylene oxide, and propylene oxide. The ability to regulate the type of alkylene oxide and amount present in the silicone polymer results in a series of products ranging widely in water/oil solubility. The technology used to produce the compounds of the present invention is very flexible and allows us to prepare performance tailored molecules for specific applications.

OBJECT OF THE INVENTION

It is the object of the present invention to provide a process for the preparation of stable emulsions and microemulsions of oils in water using as an emulsifier a series of novel phosphated silicone polymers.

It is another objective of the current invention to provide emulsion compositions which are based upon oil, water and the phosphated silicone polymers. These emulsions are dermatologically acceptable, and are for topical application. They are oil-in-water emulsions which possess stability, highly acceptable aesthetics, and can be produced without heat.

The compositions of this invention are useful for pigmented and non-pigmented systems which may contain medicaments, sunscreens, skin protectants, or hair conditioning agents.

DESCRIPTION OF THE ARTS AND PRACTICES

Silicone oils (polydimethylsiloxane) have been known to be active at the surface of plastic, cellulosic and synthetic fibers as well as paper. Despite the fact that they are lubricants that are stable to oxidation, their high cost and lack of durability has made them cost prohibitive in most application areas. Silicone oils need to be emulsified prior to application. This requires the use of not only high pressure equipment, but surface active agents which until the present invention were based upon fatty chemistry. Emulsions prepared using fatty surfactants results in the oil being dispersed in a fatty micelle. Micelles are basically small spheres in which the oil phase is contained. The micelle is dispersed into the water phase. Emulsions of this type "deliver" their oil phases by a breaking of the micelle. This can occur as the emulsion drys out when applied to the surface of a substrate being treated. The oil is released and the substrate is coated. A major difficulty with this type of delivery system is that the fatty surfactant is likewise delivered to the surface of the substrate, resulting in incomplete delivery and poor continuity of the surface coat.

U.S. Pat. No. 5,070,171 to O'Lenick, Jr. discloses the preparation of certain silicone phosphate compounds useful as raw materials in the preparation of the compositions of the present invention.

U.S. Pat. No. 5,091,483 to O'Lenick, Jr. discloses certain silicone phosphate quats which are useful as surface active agents.

U.S. Pat. No. 5,093,452 to O'Lenick, Jr. discloses certain silicone phosphate salts which are useful as fiber conditioners and antistats.

Many attempts have been made to overcome these problems and obtain an emulsion which delivers the oil without delivering a surfactant which destroys the continuity of the oil film.

THE INVENTION

SUMMARY OF THE INVENTION

The present invention relates to a process for the preparation of a oil in water emulsion based upon a series of novel phosphated silicone polymers. These phosphated silicone polymers are the topic of U.S. Pat. No. 5,070,171 issued in December 1991 to O'Lenick which have a pendant phosphate functional group present. In addition to the described ability to deposit on fiber surfaces and form effective nonvolatile surface modifying finishes. The compounds of that invention were surprisingly found to be outstanding emulsifiers for a variety of water insoluble materials collectively called oils.

The invention also relates to a composition which makes up the stable emulsion. The composition comprises (1) an oil phase selected from the group consisting of fatty triglycerides, diacylglycerides or monoacylglycerides; esters, hydrocarbons, linear and cyclic polydimethylsiloxanes; and fatty alcohols.

(2) A silicone phosphate ester as described in U.S. Pat. No. 5,070,171 which is represented by the following formula;

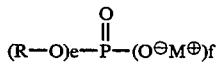

wherein
R is

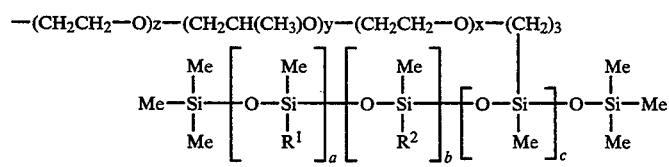

Me is methyl;
a is an integer from 0 to 200;

b is an integer from 0 to 200;
c is an integer from 1 to 200;
$R^1$ is methyl;
$R^2$ is —$(CH_2)_3$—$(OCH_2CH_2)x$—$(OCH_2CH(CH_3))y$—$(OCH_2CH_2)z$—OH;
x, y and z are integers and are independently ranging from 0 to 20 with the proviso that x+y+z is greater than or equal to 3;
e and f range from 1 to 2 with the proviso that e+f=3;
M is selected from the group consisting of H, Na, K, Li, NH4 and N—$(CH_2$—$CH_2$—$OH)_3$ and
(3) water.

We have discovered surprisingly that one can produce stable, aesthetically pleasing oil-in-water emulsions where the primary emulsifier is a silicone based phosphate ester, which has been neutralized with any of the following sodium hydroxide, potassium hydroxide, or triethanolamine or combination.

U.S. Pat. No. 5,070,171 is incorporated herein by reference. The phosphated silicone polymers are products of commerce marketed under the Pecosil trade name by Phoenix Chemical of Somerville, N.J.

In a preferred embodiment the process of the present invention is carried out using a homogenizer.

In another preferred embodiment the process of the present invention is carried out using a homogenizer operated at a pressure of between 3,000 and 6,000 psi.

In another preferred embodiment the process of the present invention is carried out using a colloid mill.

In a preferred embodiment the composition of the present invention is as follows;
(1) contains between 5% and 70% of the oil phase which is selected from the group consisting of fatty triglycerides, diacylglycerides or monoacylglycerides; esters, hydrocarbons linear and cyclic polydimethylsiloxanes and fatty alcohols or fatty alcohol alkoxylates.
(2) contains between 0.5% and 20% silicone phosphate ester emulsifier
(3) contains between 29.5% and 75% water.

In a more preferred embodiment the composition of the present invention is as follows;
(1) contains between 50% and 70% of the oil phase which is selected from the group consisting of fatty triglycerides, diacylglycerides or monoacylglycerides; esters, hydrocarbons linear and cyclic polydimethylsiloxanes; and fatty alcohols or fatty alcohol alkoxylates.
(2) contains between 1.0% and 10% silicone phosphate ester emulsifier
(3) contains between 40% and 29% water.

The preferred dimethicone coplyol phosphate has a molecular weight of 1,500–10,000, and in a more preferred embodiment has an average molecular weight of between 3,500–5,500.

The silicone phosphate compounds and some amine salts are disclosed in a patent to O'Lenick, Jr. (U.S. Pat. No. 5,093,452) were previously recognized as water-soluble or water-dispersible emollients, and conditioners. It was not until the present invention that these materials were recognized as primary oil-in-water emulsifiers.

Sodium hydroxide, potassium hydroxide, and triethanolamine were evaluated as agents for Dimethicone Copolyol Phosphate salt formation and were found to adequately accomplish the task of forming the primary oil-in-water emulsifier.

The preferred base is triethanolamine, present at a ratio from 4:1–9:1 (Dimethicone Copolyol Phosphate: Triethanolamine) more preferably 6:1.

The preferred ratio for Dimethicone copolyol Phosphate: sodium hydroxide is 15:1–35:1, more preferably 25:1, and the preferred ratio for Dimethicone Copolyol Phosphate: potassium hydroxide is 10:1–30:1, more preferably 20:1.

The resulting compositions produced are anionic oil-in-water emulsions having a pH range of about 4–9, preferably 5–6.

The preferred emulsions contain an oil phase selected from the group consisting of; triglycerides, e.g. Meadowfoam Seed Oil, Borage Seed Oil, Macadamia Nut Oil; monoacylglycerols; esters, e.g. Behenyl Behenate, Isostearyl Behenate, Octyl Palmitate; hydrocarbons; linear and cyclic polydimethylsiloxanes; and fatty alcohols. Optionally, external phase thickeners/stabilizers can be added. Such materials are known in the art and are selected from the group consisting of magnesium aluminum silicate, xanthan gum, hydroxypropyl guar and carbomer.

The preferred skin-protectant-containing formulas utilize Dimethicone, Allantoin, and/or Petrolatum and have a Dimethicone Copolyol Phosphate concentration of 1.5–5.5 percent, more preferably 2–4 percent.

The preferred medicament formulas contain anti-inflammatory steroids, anti-pruritic Hydrocortisone Acetate, and have a Dimethicone Copolyol Phosphate concentration of 1.5–5.5 percent, more preferably 2–4 percent.

The sunscreen compositions may utilize one or more sunscreening agents recognized under the Tentative Final Monograph of the Federal Register, vol. 43, no. 166, pages 38206 to 38269, entitled "Sunscreen Drug Products for Over-The-Counter Human Drugs."

The hair-conditioning formulas may contain compounds known to those familiar with the art to facilitate wet combing and dry combing of the hair.

Various optional components may be included in the formula such as fragrances; preservatives, e.g. parabens and diazolidinyl urea; pigments; dyes; propellants; viscosity control agents; humectants, e.g. propylene glycol and glycerin; or other materials that may be deemed desirable.

RAW MATERIAL EXAMPLES

Oils

The following materials are typical of the types of materials referred to as oils for the preparation of the emulsions of the present invention.

Fatty Triglycerides

These materials are generally referred to as fats. The conform to the following general structure;

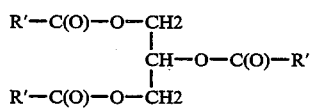

These materials are glycerine esters and are either synthetic or products of nature. Typical oils are Meadowfoam Seed Oil, Borage Seed Oil, Macadamia Nut Oil, Tallow and Soybean Oil.

Compounds in which one or two of the ester functionalities is replaced by a free hydroxyl group makes up another class of useful oils.

$$\begin{array}{l} H-O-CH_2 \\ \phantom{H-O-}| \\ \phantom{H-O}CH-O-C(O)-R' \\ \phantom{H-O-}| \\ H-O-CH_2 \end{array}$$

Monoglyceride $$\begin{array}{l} H-O-CH_2 \\ \phantom{H-O-}| \\ \phantom{H-O}CH-O-C(O)-R' \\ \phantom{H-O-}| \\ \phantom{H-O}CH_2-O-C(O)-R' \end{array}$$

Diglyceride

The triglycerides are referred to as "oils" and are generally defined by the source of the oil some examples are;

| | |
|---|---|
| Meadowfoam Sed oil | Coconut oil |
| Safflower oil | Soybean oil |
| Corn oil | Borage seed oil |
| Macadamia nut oil | |

All these materials are well defined chemicals which are items of commerce and are commercially available from Cascade Chemical Co. Park Ridge, N.J.

Fatty Esters

These materials are the reaction product of fatty acids and fatty alcohols. They conform to the following structure;

$$R''-C(O)-O-R''$$

These materials are items of commerce and are commercially available from Phoenix Chemical Inc. Somervile, N.J.

Typical compounds are;

| Trade Name | Chemical Name |
|---|---|
| Pelemol GS | Glyceryl Stearate |
| Pelemol 2022 | Octyldodecyl Behenate |
| Pelemol TGC | Octyldodecyl Citrate |
| Pelemol BB | Behenyl Behenate |
| Pelemol OPG | Octyl Pelargonate |
| Pelemol OP | Octyl Palmitate |
| Pelemol ISL | Isostearyl Lactate |

Pelemol is the registered trade mark of Phoenix Chemical Inc.

Hydrocarbons

These materials are alkanes and generally conform to the following structure;

$$CH_3-(CH_2)_q-CH_3$$

q is an integer from 8-20.

| Chemical Name | "q" Value |
|---|---|
| Decane | 8 |
| Dodeacane | 10 |
| Octyldecane | 16 |
| Octyldodecane | 18 |

Linear and Cyclic Polydimethylsiloxanes

Linear polydimethylsiloxanes conform to the following generic structure;

$$\begin{array}{c} Me \\ | \\ Me-Si- \\ | \\ Me \end{array} \begin{bmatrix} Me \\ | \\ O-Si- \\ | \\ Me \end{bmatrix}_n \begin{array}{c} Me \\ | \\ O-Si-Me \\ | \\ Me \end{array}$$

wherein Me is methyl.

Typical are products marketed by Siltech Inc. of Norcross Ga. who markets the following fluids;

| | Regular Viscosity Fluids | |
|---|---|---|
| Siltech Name | Viscosity 25 C (Centistokes) | Approximate Molecular Weight |
| Siltech F-500 | 500 | 17,250 |
| Siltech F-10,000 | 10,000 | 62,700 |
| Siltech F-60,000 | 60,000 | 116,500 |

Siltech is a registered trademark of Siltech Inc. Norcross Ga.

Fatty Alcohols

These materials generally conform to the following structure and are items of commerce available from Phoenix Chemical Somerville N.J.;

$$R''-O-H$$

Silicone Phosphate Emulsifier Compounds

The silicone phosphate compounds are made by using the technology described in U.S. Pat. No. 5,070,171 issued to O'Lenick, Jr. incorporated herein by reference.

| Example | O'Lenick Example | Base Type | x | y | z |
|---|---|---|---|---|---|
| 1 | 25 | KOH | 3 | 0 | 0 |
| 2 | 26 | NaOH | 9 | 27 | 3 |
| 3 | 27 | LiOH | 11 | 3 | 0 |
| 4 | 28 | NH4OH | 0 | 0 | 0 |
| 5 | 29 | KOH | 20 | 20 | 20 |
| 6 | 30 | NaOH | 20 | 0 | 0 |
| 7 | 31 | KOH | 10 | 10 | 10 |
| 8 | 32 | NaOH | 3 | 0 | 0 |
| 9 | 33 | KOH | 9 | 27 | 3 |
| 10 | 34 | NaOH | 11 | 3 | 0 |
| 11 | 35 | KOH | 0 | 0 | 0 |
| 12 | 36 | NaOH | 20 | 20 | 20 |
| 13 | 37 | KOH | 20 | 0 | 0 |
| 14 | 38 | NaOH | 10 | 10 | 10 |

Emulsion Examples

Example 15

To 45.0 grams of glyceryl monostearate (the oil phase) is added 10.0 grams of silicone emulsifier (Example 1) with good agitation. Next enough water is added to the mixture to result in 50% solid (in this case 55.0 grams). The resulting milky mixture is then passed through a Matin Gaulin Homogenizer at 5,000 psi three times.

Examples 16-85

Each of the examples shown are cut with water to 50% solids with water and passed through a homogenizer as specified in example 15.

The emulsions are rated for stability using the following rating system—0 Splits-5 Most Stable

| Example | Oil Phase Grams / Type | | Silicone Emulsifier Grams / Example | Stability |
|---|---|---|---|---|
| 16 | 45.0 | Glyceryl monostearate | 5.0  1 | 3 |
| 17 | 45.0 | Octyldodecyl behenate | 5.0  2 | 3 |
| 18 | 45.0 | Octyldodecyl citrate | 5.0  3 | 4 |
| 19 | 45.0 | Behenyl behenate | 5.0  4 | 0 |
| 20 | 45.0 | Octyl Pelagornate | 5.0  5 | 3 |
| 21 | 45.0 | Octyl Palmitate | 5.0  6 | 4 |
| 22 | 45.0 | Isostearyl Lactate | 5.0  7 | 3 |
| 23 | 45.0 | Glyceryl monostearate | 10.0  8 | 3 |
| 24 | 45.0 | Octyldodecyl behenate | 10.0  9 | 3 |
| 25 | 45.0 | Octyldodecyl citrate | 10.0  10 | 4 |
| 26 | 45.0 | Behenyl behenate | 10.0  11 | 0 |
| 27 | 45.0 | Octyl Pelagornate | 10.0  12 | 3 |
| 28 | 45.0 | Octyl Palmitate | 10.0  13 | 4 |
| 29 | 45.0 | Isostearyl Lactate | 10.0  14 | 4 |

The compounds that failed to emulsify were based upon the dimethicone copolyol phosphate which contained no alkylene oxide as follows;

| Example | Stability | Base | x | y | z |
|---|---|---|---|---|---|
| 4 | 0 | NH4OH | 0 | 0 | 0 |
| 11 | 0 | KOH | 0 | 0 | 0 |

Therefore ethylene oxide is required obtain an emulsion.

Silicone Compounds

| Example | Oil Phase Grams / Type | | Silicone Emulsifier Grams / Example | Stability |
|---|---|---|---|---|
| 30 | 45.0 | F-500 | 5.0  1 | 3 |
| 31 | 45.0 | F-500 | 5.0  2 | 3 |
| 32 | 45.0 | F-500 | 5.0  3 | 4 |
| 33 | 45.0 | F-500 | 5.0  4 | 0 |
| 34 | 45.0 | F-500 | 5.0  5 | 3 |
| 35 | 45.0 | F-500 | 5.0  6 | 4 |
| 36 | 45.0 | F-500 | 5.0  7 | 3 |
| 37 | 45.0 | F-10,000 | 10.0  8 | 3 |
| 38 | 45.0 | F-10,000 | 10.0  9 | 3 |
| 39 | 45.0 | F-10,000 | 10.0  10 | 4 |
| 40 | 45.0 | F-10,000 | 10.0  11 | 0 |
| 41 | 45.0 | F-10,000 | 10.0  12 | 3 |
| 42 | 45.0 | F-10,000 | 10.0  13 | 4 |
| 43 | 45.0 | F-10,000 | 10.0  14 | 4 |

The compounds that failed to emulsify silicone oil were based upon the dimethicone copolyol phosphate which contained no alkylene oxide as follows;

| Example | Stability | Base | x | y | z |
|---|---|---|---|---|---|
| 4 | 0 | NH4OH | 0 | 0 | 0 |
| 11 | 0 | KOH | 0 | 0 | 0 |

Therefore ethylene oxide is required obtain an emulsion.

Hydrocarbon Compounds

| Example | Oil Phase Grams / Type | | Silicone Emulsifier Grams / Example | Stability |
|---|---|---|---|---|
| 44 | 45.0 | Decane | 5.0  1 | 3 |
| 45 | 45.0 | Decane | 5.0  2 | 3 |
| 46 | 45.0 | Decane | 5.0  3 | 4 |
| 47 | 45.0 | Decane | 5.0  4 | 0 |
| 48 | 45.0 | Decane | 5.0  5 | 3 |
| 49 | 45.0 | Decane | 5.0  6 | 4 |
| 50 | 45.0 | Dodecane | 5.0  7 | 3 |
| 51 | 45.0 | Dodecane | 10.0  8 | 3 |
| 52 | 45.0 | Dodecane | 10.0  9 | 3 |
| 53 | 45.0 | Dodecane | 10.0  10 | 4 |
| 54 | 45.0 | Dodecane | 10.0  11 | 0 |
| 55 | 45.0 | Octyldecane | 10.0  12 | 3 |
| 56 | 45.0 | Dodecane | 10.0  13 | 4 |
| 57 | 45.0 | Octyldodecane | 10.0  14 | 4 |

The compounds that failed to emulsify hydrocarbon were based upon the dimethicone copolyol phosphate which contained no alkylene oxide as follows;

| Example | Stability | Base | x | y | z |
|---|---|---|---|---|---|
| 4 | 0 | NH4OH | 0 | 0 | 0 |
| 11 | 0 | KOH | 0 | 0 | 0 |

Therefore ethylene oxide is required obtain an emulsion.

Fatty Alcohol Alkoxylates

| Example | Oil Phase Grams / Type | | Silicone Emulsifier Grams / Example | Stability |
|---|---|---|---|---|
| 58 | 45.0 | Cetyl | 5.0  1 | 3 |
| 59 | 45.0 | Cetyl | 5.0  2 | 3 |
| 60 | 45.0 | Cetyl | 5.0  3 | 4 |
| 61 | 45.0 | Stearyl | 5.0  4 | 0 |
| 62 | 45.0 | Stearyl | 5.0  5 | 3 |
| 63 | 45.0 | Stearyl | 5.0  6 | 4 |
| 64 | 45.0 | Myristyl | 5.0  7 | 3 |
| 65 | 45.0 | Myristyl | 10.0  8 | 3 |
| 66 | 45.0 | Myristyl | 10.0  9 | 3 |
| 67 | 45.0 | Lauryl | 10.0  10 | 4 |
| 68 | 45.0 | Lauryl | 10.0  11 | 0 |
| 69 | 45.0 | Lauryl | 10.0  12 | 3 |
| 70 | 45.0 | Steryl | 10.0  13 | 4 |
| 71 | 45.0 | Lauryl | 10.0  14 | 4 |

The compounds that failed to emulsify alcohol alkoxylate were based upon the dimethicone copolyol phosphate which contained no alkylene oxide as follows;

| Example | Stability | Base | x | y | z |
|---|---|---|---|---|---|
| 4 | 0 | NH4OH | 0 | 0 | 0 |
| 11 | 0 | KOH | 0 | 0 | 0 |

Therefore ethylene oxide is required obtain an emulsion.

| Example | Oil Phase Grams / Type | | Silicone Emulsifier Grams / Example | | Stability |
|---|---|---|---|---|---|
| 72 | 45.0 | Soybean | 5.0 | 1 | 3 |
| 73 | 45.0 | Soybean | 5.0 | 2 | 3 |
| 74 | 45.0 | Soybean | 5.0 | 3 | 4 |
| 75 | 45.0 | Corn | 5.0 | 4 | 0 |
| 76 | 45.0 | Corn | 5.0 | 5 | 3 |
| 77 | 45.0 | Meadowfoam | 5.0 | 6 | 4 |
| 78 | 45.0 | Coconut | 5.0 | 7 | 3 |
| 79 | 45.0 | Coconut | 10.0 | 8 | 3 |
| 80 | 45.0 | Coconut | 10.0 | 9 | 3 |
| 81 | 45.0 | Coconut | 10.0 | 10 | 4 |
| 82 | 45.0 | Coconut | 10.0 | 11 | 0 |
| 83 | 45.0 | Borage oil | 10.0 | 12 | 3 |
| 84 | 45.0 | Soybean | 10.0 | 13 | 4 |
| 85 | 45.0 | Soybean | 10.0 | 14 | 4 |

The compounds that failed to emulsify alcohol alkoxylate were based upon the dimethicone copolyol phosphate which contained no alkylene oxide as follows;

| Example | Stability | Base | x | y | z |
|---|---|---|---|---|---|
| 4 | 0 | NH4OH | 0 | 0 | 0 |
| 11 | 0 | KOH | 0 | 0 | 0 |

Therefore ethylene oxide is required obtain an emulsion.

What is claimed:

1. A process for preparing an oil in water emulsion which comprises;
   (a) mixing an oil selected from the group consisting of esters, hydrocarbons, polydimethylsiloxanes; and fatty alcohols;
   with effective emulsifying concentration of a silicone based phosphate ester conforming to the following structure;

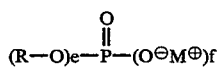

wherein;
R is

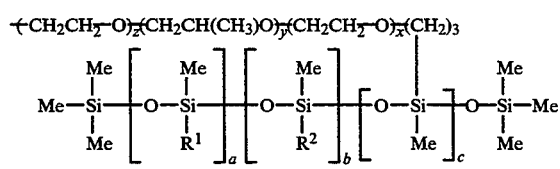

Me is methyl;
a is an integer from 0 to 200;
b is an integer from 0 to 200;
c is an integer from 1 to 200;
$R^1$ is methyl;
$R^2$ is $-(CH_2)_3-(OCH_2CH_2)_x-(OCH_2CH(CH_3))_y-(OCH_2CH_2)_z-OH$;
x, y and z are integers and are independently ranging from 0 to 20 with the proviso that x+y+x is greater than or equal to 3;
e and f range from 1 to 2 with the proviso that e+f=3;
M is selected from the group consisting of H, Na, K, Li, NH4 and $N-(CH_2-CH_2-OH)_3$
(b) subsequently adding water; and in a final optional step
(c) homogenizing the resulting mixture.

2. A process of claim 1 wherein said oil is a hydrocarbon.

3. A process of claim 1 wherein said oil is a linear and cyclic polydimethylsiloxanes.

4. A process of claim 1 wherein said oil is a fatty alcohol.

5. A process of claim 1 wherein said oil is a fatty alcohol alkoxylate.

6. An emulsion composition which comprises;
   (1) an oil phase selected from the group consisting of esters, hydrocarbons, polydimethylsiloxanes and fatty alcohols;
   (2) A silicone based phosphate ester which conforms to the following formula;

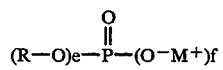

wherein;
R is

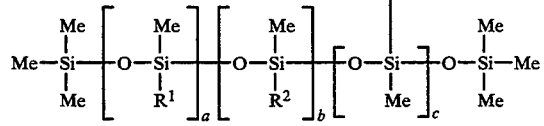

Me is methyl;
a is an integer from 0 to 200;
b is an integer from 0 to 200;
c is an integer from 1 to 200;
$R^1$ is methyl;
$R^2$ is $-(CH_2)_3-(OCH_2CH_2)_x-(OCH_2CH(CH_3))_y-(OCH_2CH_2)_z-OH$;
x, y and z are integers and are independently ranging from 0 to 20 with the proviso that x+y+z is greater than or equal to 3;
e and f range from 1 to 2 with the proviso that e+f=3;
M is selected from the group consisting of H, Na, K, Li, NH4 and $N-(CH_2-CH_2-OH)_3$ and
(3) water.

7. A composition of claim 6 wherein said oil is a hydrocarbon.

8. A composition of claim 6 wherein said oil is a polydimethylsiloxanes.

9. A composition of claim 6 wherein said oil is a fatty alcohol.

10. A composition of claim 6 wherein said oil is a fatty alcohol alkoxylate.

* * * * *